US012788638B2

(12) United States Patent
Nagata

(10) Patent No.: US 12,788,638 B2
(45) Date of Patent: Nov. 10, 2026

(54) METHOD AND APPARATUS FOR MANUFACTURING DISPOSABLE WEARABLE ARTICLES

(71) Applicant: ZUIKO CORPORATION, Ibaraki (JP)

(72) Inventor: Kazuma Nagata, Ibaraki (JP)

(73) Assignee: ZUIKO CORPORATION, Ibaraki (JP)

( * ) Notice: Subject to any disclaimer, the term of this patent is extended or adjusted under 35 U.S.C. 154(b) by 310 days.

(21) Appl. No.: 18/689,380

(22) PCT Filed: Aug. 31, 2022

(86) PCT No.: PCT/JP2022/032708
§ 371 (c)(1),
(2) Date: Mar. 5, 2024

(87) PCT Pub. No.: WO2023/037938
PCT Pub. Date: Mar. 16, 2023

(65) Prior Publication Data

US 2024/0398632 A1 Dec. 5, 2024

(30) Foreign Application Priority Data

Sep. 7, 2021 (JP) ................................ 2021-145224

(51) Int. Cl.
*A61F 13/15* (2006.01)
*A61F 13/494* (2006.01)

(52) U.S. Cl.
CPC .. *A61F 13/15764* (2013.01); *A61F 13/15804* (2013.01); *A61F 13/49413* (2013.01)

(58) Field of Classification Search
CPC .......... A61F 13/15764; A61F 13/15804; A61F 13/49413; A61F 13/494
See application file for complete search history.

(56) References Cited

U.S. PATENT DOCUMENTS

2002/0125105 A1* 9/2002 Nakakado ............ B65G 47/848 198/471.1
2008/0289468 A1 11/2008 Nakakado et al.
2013/0213570 A1* 8/2013 Iida .......................... B65H 5/00 156/538

FOREIGN PATENT DOCUMENTS

JP 2000513954 A 10/2000
JP 2012045317 A 3/2012
(Continued)

OTHER PUBLICATIONS

English-language translation of International Preliminary Report on Patentability issued in connection with underlying International Application PCT/JP2022/032708.
(Continued)

*Primary Examiner* — George R Koch
(74) *Attorney, Agent, or Firm* — United IP Counselors, LLC

(57) ABSTRACT

A method of manufacturing disposable wearable articles includes: a step of carrying in a continuous direction a first continuous web for forming pocket members; a step of forming a pocket web by placing a first elastic member in a stretched state on the first continuous web; a cutting step of successively cutting the pocket web to obtain pocket members with a predetermined length; an orientation changing step of changing the orientation of the pocket members by turning the pocket member so that a carrying direction of the pocket member aligns with a width direction of the pocket member; a repitch step of increasing a spacing between mutually adjacent pocket members; and a placement step of placing the pocket members across a pair of three-dimensional gathers, wherein the cutting step, the orientation changing step, and the placement step are performed on a suction drum.

5 Claims, 2 Drawing Sheets

(56) References Cited

FOREIGN PATENT DOCUMENTS

| | | | | | |
|---|---|---|---|---|---|
| JP | 2013255624 | A | * | 12/2013 | |
| JP | 2020171421 | A | * | 10/2020 | ............. A61F 13/49 |
| WO | 9715260 | A1 | | 5/1997 | |
| WO | 2001044086 | | | 6/2001 | |
| WO | 2005075163 | A1 | | 8/2005 | |

OTHER PUBLICATIONS

English-language translation of International Search Report issued in connection with underlying International Application PCT/JP2022/032708.

* cited by examiner

METHOD AND APPARATUS FOR MANUFACTURING DISPOSABLE WEARABLE ARTICLES

TECHNICAL FIELD

The present invention relates to a method and apparatus for manufacturing disposable wearable articles having leak-proof pockets.

BACKGROUND ART

Conventionally, placing a laterally long pocket member in the waistband portion of a disposable wearable article to prevent, by means of a pocket, leakage of waste from the waistband portion has been proposed (Patent Document 1).

CITATION LIST

Patent Literature

Patent Document 1: Japanese National Publication 2000-513954 (front page)

SUMMARY OF INVENTION

On the laterally long pocket member, thread rubber that stretches and contracts around the waist is placed. At the same time, on three-dimensional gathers that form part of the body of the wearable article, thread rubber that stretches and contracts in a longitudinal direction is placed. Consequently, when the two are superposed and the pocket member is placed on the three-dimensional gathers, defects such as the occurrence of wrinkles in the pocket member are likely to occur.

However, the above document discloses nothing in regard to the process of placing the pocket member.

Consequently, it is an object of the present invention to provide a method and apparatus for manufacturing disposable wearable articles with which pocket members are less likely to wrinkle and the pocket members can be efficiently placed.

The method of the present invention includes:

a step of carrying in a continuous direction a first continuous web W1 for forming pocket members P;

a step of forming a pocket web Wp by placing a first elastic member F1 in a stretched state on the first continuous web W1;

a cutting step of successively cutting a leading end portion of the pocket web Wp to obtain pocket members P with a predetermined length;

an orientation changing step of changing the orientation of the pocket member P by turning the pocket member P so that a carrying direction of the pocket member P aligns with a width direction of the pocket member P;

a repitch step of increasing a spacing between mutually adjacent pocket members P; and a placement step of placing the pocket member P across a pair of three-dimensional gathers G, the cutting step, the orientation changing step, and the placement step are performed on a suction drum.

The apparatus of the present invention includes:

a first folder H1 configured to form a pocket web Wp by folding over a first continuous web W1, on which a first elastic member F1 in a stretched state is placed, by folding the first continuous web W1 along a virtual fold line L extending along a carrying direction so that the first elastic member F1 is sandwiched in the folded-over first continuous web W1;

a cutter C configured to successively cut a leading end portion of the pocket web Wp to form pocket members P;

a turn drum D1 configured to suck and hold the pocket web Wp before it is cut by the cutter C, configured to suck and hold the pocket member P formed as a result of cutting the pocket web Wp with the cutter C, and configured to change the orientation of the pocket member P by turning the pocket members P 90° so that a carrying direction of the pocket member P aligns with a width direction of the pocket member P;

a repitch drum D2 configured to suck and successively receive the pocket members P from the turn drum D1 and increase the spacing between mutually adjacent pocket members P; and a placement drum D3 configured to suck and carry a gathered web W21 having three-dimensional gathers G, in which second elastic members F2 are stretched and extended, in a stretched state and configured to successively receive on the gathered web W21 the pocket members P from the repitch drum D2.

According to the present invention, as the formation and placement of the pocket members are performed on the suction drum, it is easy to maintain a state in which the elastic members are stretched. Consequently, the pocket members are less likely to wrinkle and efficient placement is possible.

DESCRIPTION OF EMBODIMENTS

The present invention will become more clearly understood from the following description of preferred embodiments reference to the accompanying drawings. However, the embodiments and the drawings are simply for the purpose of illustration and explanation and are not to be utilized to determine the scope of the present invention. The scope of the present invention is to be determined based solely on the claims. In the accompanying drawings, the same parts numbers in multiple views refer to the same or corresponding parts.

Figure 1:
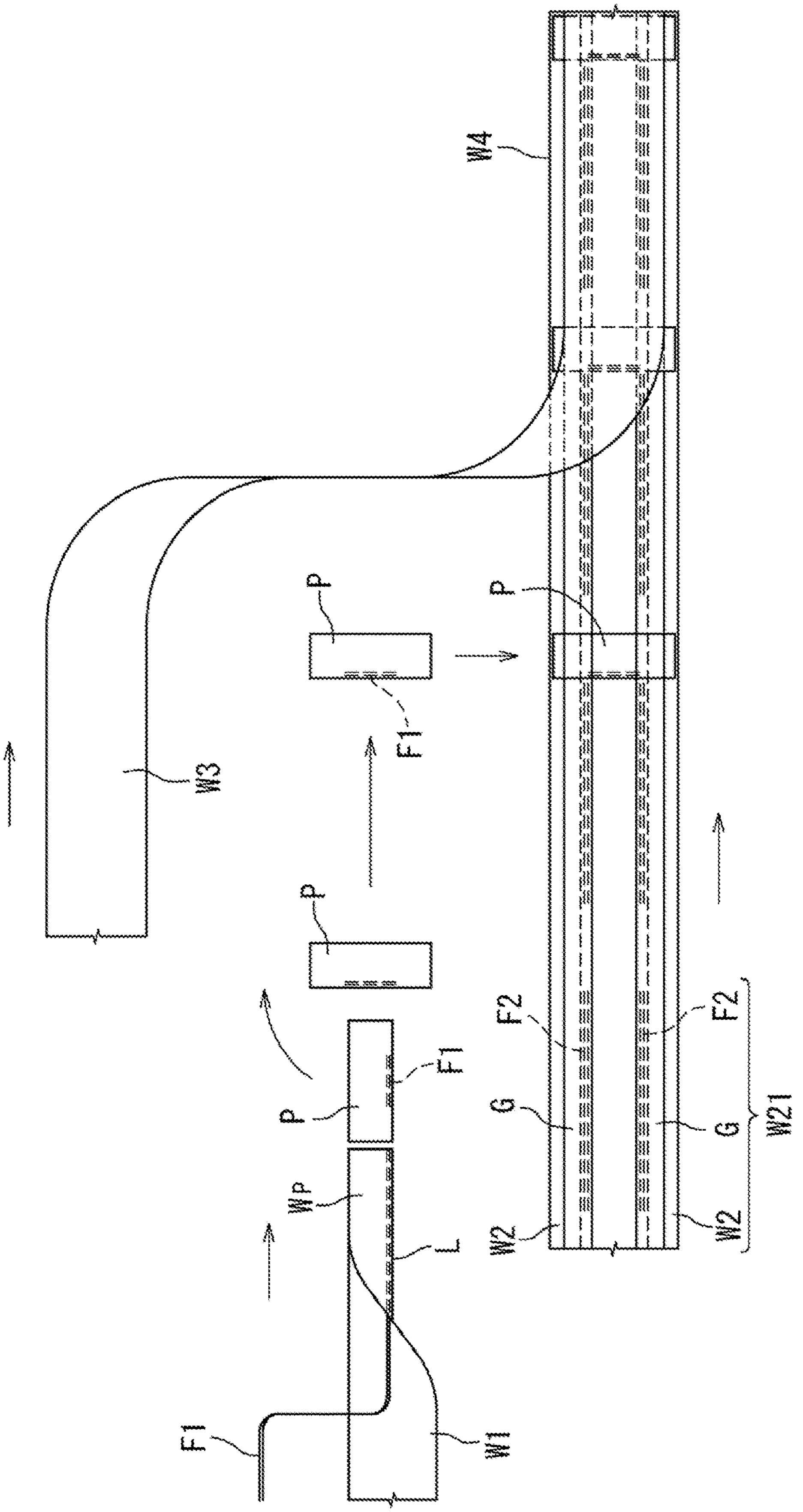
FIG. 1 is a conceptual diagram showing an embodiment of the method of the present invention.
Figure 2:
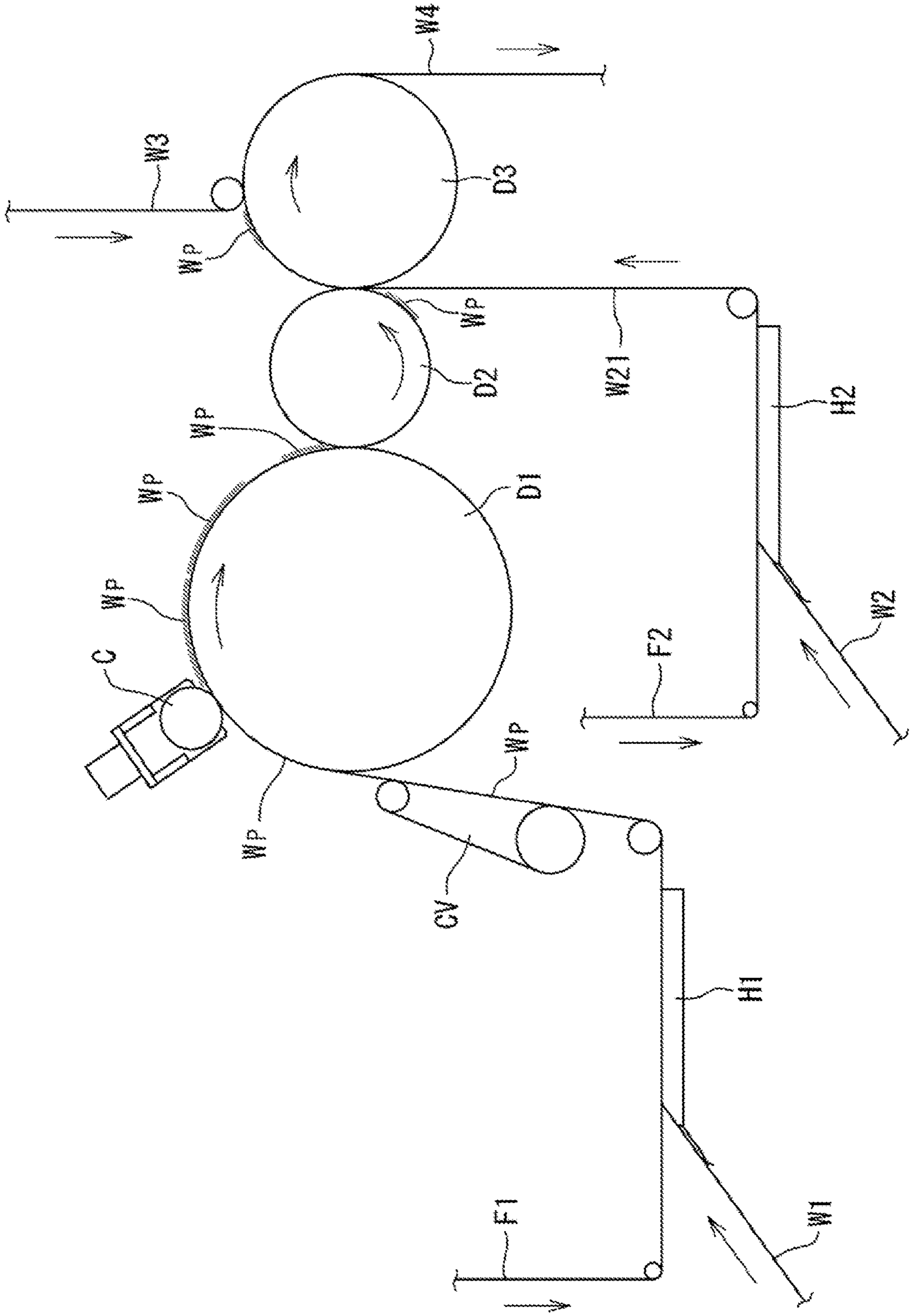
FIG. 2 is a schematic layout diagram showing an embodiment of the apparatus of the present invention.

An embodiment of the present invention will be described below in accordance with the drawings FIG. 1 to FIG. 2 show one embodiment. First, the manufacturing method will be described.

As shown in FIG. 1, while carrying a first continuous web W1 for forming pocket members P in a continuous direction, a pocket web Wp is formed by placing a first elastic member F1 in a stretched state on the first continuous web W1.

At this time, the pocket web Wp is formed by folding over the first continuous web W1, on which the first elastic member F1 has been placed, by folding the first continuous web W1 along a virtual fold line L extending along the carrying direction so that the first elastic member F1 is sandwiched in the folded-over first continuous web W1 and joining the first elastic member F1 to the folded-over first continuous web W1.

After this formation, in a subsequent cutting step, a leading end portion of the pocket web Wp is successively cut to obtain pocket members P with a predetermined length. After this cutting step, a subsequent orientation changing step and placement step are executed.

In the orientation changing step, the orientation of the pocket members P is changed by turning the pocket members P 90° so that a carrying direction of the pocket members P aligns with a width direction of the pocket members P. Thereafter, in a repitch step, the spacing between mutually adjacent pocket members P is increased to correspond to units of wearable articles.

In the case of this example, the repitch step of increasing the spacing between mutually adjacent pocket members P is performed after the carrying direction of the pocket members P has been aligned with the width direction of the pocket members P in the orientation changing step.

It will be noted that the orientation changing step may also be executed after the repitch step.

Thereafter, the placement step, in which the pocket members P are placed on a gathered web W21 having a pair of three-dimensional gathers G, is executed. The gathered web W21 has the pair of three-dimensional gathers G which are continuous in the carrying direction.

Each of the three-dimensional gathers G has a second elastic member F2 in a site of the folded web and, as is well known, stands upright when worn to inhibit lateral leakage of waste.

After the placement, a continuous layered body W4 that becomes a part of the bodies of the wearable articles is formed as a result of a third continuous web W3 being placed along the center of the gathered web W21 so as to cover each of the pocket members P.

The cutting step, the orientation changing step, and the placement step are performed on three drums D1 to D3 of FIG. 2 as described below. An example of the manufacturing apparatus will be described below.

In FIG. 2, the first continuous web W1 and the first elastic member F1 are introduced to a first folder H1. The first folder H1 forms the pocket web Wp by folding over the first continuous web W1, on which the first elastic member F1 is placed, by folding the first continuous web W1 along a virtual fold line L extending along a carrying direction (FIG. 1) so that the first elastic member F1 is sandwiched in the folded-over first continuous web W1.

The pocket web Wp is carried at a fixed speed by a conveyor CV and introduced onto a turn drum D1. The turn drum D1 has a plurality of anvils and pads, and on the turn drum D1 a cutter C successively cuts the leading end portion the pocket web Wp to successively form the pocket members P (FIG. 1).

The turn drum D1 uses a well-known structure to turn the orientation of the pads 90° after the cutting. That is, the turn drum D1 sucks and holds the pocket web Wp before it is cut by the cutter C, sucks and holds the pocket member P formed as a result of cutting the pocket web Wp with the cutter C, and changes the orientation of the pocket member P by turning the pocket member P 90° so that the carrying direction of the pocket member P aligns with the width direction of the pocket member P. Examples of such a turn drum D1 include the drum disclosed in WO 2005/075163 A1, and all descriptions therein are incorporated here.

A repitch drum D2 sucks and successively receives the pocket members P from the turn drum D1 and increases the spacing between mutually adjacent pocket members P. Examples of such a repitch drum D2 include the drum disclosed in WO 01/44086 A1, and all descriptions therein are incorporated here.

Meanwhile, the second continuous web W2 and the second elastic members F2 are introduced to a second folder H2. The second folder H2 forms the gathered web W21 of FIG. 1 by folding the second continuous web W2 and placing the second elastic members F2 on the folded sites. The gathered web W21 that is formed is continuously introduced to a placement drum D3 of FIG. 2.

The repitched pocket members P are placed on the gathered web W21 as it is being carried by the placement drum D3. That is, the placement drum D3 carries, while sucking in a stretched state, the gathered web W21 having the three-dimensional gathers G (FIG. 1) in an extended state and successively receives via the gathered web W21 the pocket members P on the gathered web W21. In this way, the layered body W4, in which the pocket members P are placed in units of wearable articles, is obtained.

It will be noted that the third continuous web W3 introduced to the placement drum D3 of FIG. 2 may be further layered on the layered body W4.

In this connection, the repitch drum D2 of FIG. 2 may have a structure which has a plurality of pads and uses servo motors corresponding to each of the pads to change the circumferential speeds of each of the pads and repitch the pocket members received by each of the pads. In this case, the spacing between adjacent pocket members can be increased in accordance with the size of the articles. It will be noted that examples of such a repitch drum using servo motors include the drum disclosed in JP2013-255624A (FIG. 2), and all descriptions therein are incorporated here.

The above embodiment includes the following inventions.

In a preferred manufacturing method, in the step of forming the pocket web Wp, the pocket web Wp is formed by folding over the first continuous web W1, on which the first elastic member F1 has been placed, by folding the first continuous web W1 along the virtual fold line L extending along the carrying direction so that the first elastic member F1 is sandwiched in the folded-over first continuous web W1 and joining the first elastic member F1 to the folded-over first continuous web W1.

In this case, contractile force resulting from the first elastic member F1 acts on the pocket members P, but because the pocket members P are carried and delivered on suction drums, the pocket members P are placed on the three-dimensional gathers G without contracting due to the first elastic member F1. For that reason, the pocket members P are less likely to wrinkle and efficient placement is possible.

In another preferred manufacturing method, the repitch step of increasing the spacing between mutually adjacent pocket members P is performed after the carrying direction of the pocket members P has been aligned with the width direction of the pocket members P by the orientation changing step.

By turning the pocket members P, which are long in the carrying direction, 90° to change their orientation, their length in the carrying direction becomes smaller and the diameter of the repitch drum becomes smaller.

When the repitch step is performed after the orientation changing step, the orientation change may be performed and a slight repitch may be performed by a repitch/turn drum and the spacing between the pocket members may be greatly increased by another repitch drum.

The features described and/or illustrated in association with one embodiment or preferred embodiments can be used in the same or similar form in one or more other embodiments and/or in combination with, or instead of, other embodiments.

While preferred embodiments have been described above with reference to the drawings, a variety of obvious changes and modifications will readily occur to those skilled in the art upon reading the present specification.

For example, the pocket members may be provided on both the front panel and the rear panel of one wearable article.

Furthermore, the pads and the anvils of the turn drum need not be separate bodies, and the anvils may be integrally provided on downstream ends or upstream ends of the pads.

Consequently, such changes and modifications are to be interpreted as being within the scope of the present invention as defined by the claims.

INDUSTRIAL APPLICABILITY

The present invention can be applied to a method and apparatus for manufacturing disposable wearable articles.

REFERENCE SIGNS LIST

H1: First Folder
D1: Turn Drum
D2: Repitch Drum
D3: Placement Drum
H2: Second Folder
C: Cutter
CV: Transport Conveyor
G: Three-dimensional Gather
W1: First Continuous Web
F1: First Elastic Member
Wp: Pocket Web
P: Pocket Member
L: Fold Line
W2: Second Continuous Web
F2: Second Elastic Member
W21: Gathered Web
W3: Third Continuous Web
W4: Layered Body

The invention claimed is:

1. A method of manufacturing disposable wearable articles comprising:

carrying in a continuous direction a first continuous web for forming pocket members;

forming a pocket web by placing a first elastic member in a stretched state on the first continuous web;

successively cutting a leading end portion of the pocket web to obtain pocket members with a predetermined length;

changing the orientation of the pocket members by turning the pocket members so that a carrying direction of the pocket members aligns with a width direction of the pocket member;

increasing a spacing between mutually adjacent pocket members using a repitch drum;

carrying a gathered web in a stretched state by rotating a placement drum around which the gathered web is wound, the gathered web having a pair of three-dimensional gathers disposed apart from each other and being in a stretched state;

receiving the pocket members carried by the repitch drum onto the gathered web carried by the placement drum between the repitch drum and the placement drum; and placing the pocket members across the pair of the three-dimensional gathers of the gathered web, wherein the cutting, the changing the orientation, and the placing are performed on suction drums, and the suction drums include the repitch drum and the placement drum.

2. The method of manufacturing disposable wearable articles according to claim 1, wherein in the forming the pocket web, the pocket web is formed by folding over the first continuous web, on which the first elastic member has been placed, by folding the first continuous web along a virtual fold line extending along a carrying direction of the first continuous web so that the first elastic member is sandwiched in the folded-over first continuous web and joining the first elastic member to the folded-over first continuous web.

3. The method of manufacturing disposable wearable articles according to claim 2, wherein the increasing the spacing between mutually adjacent pocket members is performed after the carrying direction of the pocket members has been aligned with the width direction of the pocket members in the changing the orientation.

4. The method of manufacturing disposable wearable articles according to claim 1, wherein the increasing the spacing between mutually adjacent pocket members is performed after the carrying direction of the pocket members has been aligned with the width direction of the pocket members in the changing the orientation.

5. An apparatus for manufacturing disposable wearable articles comprising:

a first folder configured to form a pocket web by folding over a first continuous web, on which a first elastic member in a stretched state is placed, by folding the first continuous web along a virtual fold line along a carrying direction of the first continuous web so that the first elastic member is sandwiched in the folded-over first continuous web;

a cutter configured to successively cut a leading end portion of the pocket web to form pocket members;

a turn drum configured to suck and hold the pocket web before it is cut by the cutter, configured to suck and hold the pocket members formed as a result of cutting the pocket web with the cutter, and configured to change the orientation of the pocket member by turning the pocket members 90° so that a carrying direction of the pocket members aligns with a width direction of the pocket member;

a repitch drum configured to suck and successively receive the pocket members from the turn drum and increase the spacing between mutually adjacent pocket members; and a placement drum around which a gathered web having a pair of three-dimensional gathers disposed apart from each other in which second elastic members are stretched and extended is configured to be wound and being configured to suck and carry the wounded gathered web, in a stretched state, the placement drum successively receiving on the gathered web the pocket members from the repitch drum between the repitch drum and the placement drum.

* * * * *